(12) United States Patent
Kumar

(10) Patent No.: US 10,052,336 B2
(45) Date of Patent: *Aug. 21, 2018

(54) PULMONARY INTERSTITIAL PNEUMONIA TREATMENT

(71) Applicant: Kaplesh Kumar, Wellesley, MA (US)

(72) Inventor: Kaplesh Kumar, Wellesley, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,595

(22) Filed: Feb. 9, 2017

(65) Prior Publication Data

US 2017/0151265 A1   Jun. 1, 2017

Related U.S. Application Data

(63) Continuation-in-part of application No. 14/455,605, filed on Aug. 8, 2014, now Pat. No. 9,603,857, which is a continuation-in-part of application No. 13/627,955, filed on Sep. 26, 2012.

(51) Int. Cl.
| | |
|---|---|
| *A61K 31/565* | (2006.01) |
| *A61K 31/573* | (2006.01) |
| *A61K 31/52* | (2006.01) |
| *A61K 31/616* | (2006.01) |

(52) U.S. Cl.
CPC ............ *A61K 31/573* (2013.01); *A61K 31/52* (2013.01); *A61K 31/616* (2013.01)

(58) Field of Classification Search
CPC .... A61K 31/573; A61K 31/57; A61K 31/565; A61K 31/52
USPC ............................... 514/263.2, 263.23, 263.3
See application file for complete search history.

(56) References Cited

U.S. PATENT DOCUMENTS

| | | | | |
|---|---|---|---|---|
| 9,603,857 B2 * | 3/2017 | Kumar | ................. | A61K 31/366 |
| 2013/0143852 A1 * | 6/2013 | Kumar | ................. | A61K 31/573 |
| | | | | 514/179 |

OTHER PUBLICATIONS

Idiopathic Pulmonary Fibrosis: Diagnosis and Treatment, International Consensus Statement. Am. J. Crit. Care Med vol. 161 pp. 646-664 published 2000.*

Ganesh et al (NEJM vol. 366 pp. 1968-1977 published 2012).*
Flaherty et al (Eur. Respir. J. vol. 19 pp. 275-283 published 2002) (Year: 2002).*
Jastrzebski et al (J. of Physiology and Pharmacology vol. 57 pp. 139-148 published 2006) (Year: 2006).*
G. Raghu, K. J. Anstrom, T. E. King, Jr. et al, "Prednisone, Azathioprine, and N-Acetylcysteine for Pulmonary Fibrosis," N. Engl. J. Med. 2012; 366: 1968-77.
F. J. Martinez, J. A. de Andrade, K. J. Anstrom et al, "Randomized Trial of Acetylcysteine in Idiopathic Pulmonary Fibrosis," N. Engl. J. Med. 2014; 370: 2093-101.
National Institutes of Health Press Release: "Commonly Used Three Drug Regimen ffor Idiopathic Pulmonary Fibrosis Found Harmful," Friday, Oct. 21, 2011.
P. M. Ridker, "Closing the Loop on Inflammation and Atherothrombosis," J. Am. Clin. Climatol. Assoc. 2013; 124: 174-190.
K. Kumar, "Inflammatory Disease Model and Treatment Method," JMRP 2013; 2:120-125.
C. M. Magro, W. J. Waldman, D. A. Knight et al, "Idiopathic Pulmonary Fibrosis Related to Endothelial Injury and Antiendothelial Cell Antibodies," Human Immunology 2006; 67:28.

* cited by examiner

*Primary Examiner* — Timothy P Thomas
*Assistant Examiner* — George W Kosturko
(74) *Attorney, Agent, or Firm* — Kaplesh Kumar

(57) ABSTRACT

Model and method of treating inflammatory diseases. Traditional treatments for such diseases include administering to the patient toxic anti-inflammatory drugs. Following stabilization of the symptoms, the drug doses are tapered down to minimize side effects, as a result of which inflammation remains high and the disease is rarely cured. A chemistry-based disease model concludes that irrespective of the role that inflammation plays in the disease, inflammation reduction will impede disease initiation and progression. Managing and controlling inflammatory diseases requires reducing inflammation to acceptable normal values. Non-toxic ways such as non-steroidal anti-inflammatory drugs, anti-inflammatory diets, and regular exercise allow such reduction in inflammation to normal values, thereby slowing down or arresting disease progression and allowing the discontinuation or reduction of toxic anti-inflammatory therapy while maintaining low inflammation using non-toxic therapy.

4 Claims, No Drawings

PULMONARY INTERSTITIAL PNEUMONIA TREATMENT

CROSS-REFERENCE TO RELATED APPLICATIONS

This application is a continuation-in-part of application Ser. No. 14/455,605, filed 8 Aug. 2014, entitled INFLAMMATORY DISEASE MODEL AND METHOD OF TREATMENT, which was a continuation-in-part of application Ser. No. 13/627,955, filed 26 Sep. 2012 with the same title, now abandoned.

The prior patent applications identified above are incorporated herein by reference in their entirety to provide continuity of disclosure.

FIELD OF INVENTION

The instant invention is in the general field of chronic disease initiation and progression and treatment methods for such diseases. More specifically, it is in the field of inflammatory disease initiation and progression and methods of treating them. Inflammatory diseases are those in which systemic inflammation is associated with the disease.

BACKGROUND OF INVENTION

There have been several reports in the popular media and the medical literature emphasizing the importance of diet and exercise in preventing or controlling heart disease (Ornish D. et al, Lancet 1990; 336:129-133), diabetes (Boole N. G. et al, JAMA 2001, 286:1218-1227), and dementia (Rovio S. et al, Lancet Neurology 2005, 4:705-711). Gastric bypass surgery too has been shown to control diabetes (Adams T. D. et al, N Engl J Med 2007, 357:753-761). Less publicized is the fact that these and many other chronic diseases are accompanied by systemic inflammation, which can be measured and tracked by analyzing the blood of the affected patient for CRP (C-Reactive Protein) level. (See, e.g., Hu F. B. Et al, Diabetes 2004, 53:693-70; Libby P. Nature 2002, 420:868-874; Ridker P. et al, N Engl J Med 2000, 342:836-843; Baumgart D. et al, Lancet 2007, 369:1627-1640; Balkwill F. et al, Lancet 2001, 357:539-545.)

A special issue of Technology Review (Vol. 115, No. 2, April 2012), published by the Massachusetts Institute of Technology, featured an article entitled "The Patient of the Future," which described the efforts of Internet pioneer Larry Smarr to quantify his health parameters by tracking about 100 biomarkers. An analysis of his data over time showed that from among all biomarkers tracked, the CRP level was singularly elevated above the normal range. Smarr reportedly suffered from Crohn's disease, an inflammatory bowel disease. Over seven months, his CRP level increased from a high value of 6.1 mg/l to an even higher value of 11.8 mg/l (less than 3 mg/l is the typical accepted normal range). Within a few months of reaching this higher value, Smarr suffered severe abdominal pain, which was diagnosed as acute diverticulitis, an inflammatory disease of the colon.

The traditional treatments for the vast majority of the inflammatory diseases involve administering anti-inflammatory drugs to suppress the immune response of the patient. Nearly all of such drugs, which are mostly steroidal and generally toxic, come with unacceptable side effects. This concern limits drug usage to the minimum total doses that will suppress the symptoms at an appropriate level. Following stabilization of the symptoms, the drug doses are quickly tapered down at a prescribed schedule to minimize side effects, the consequence of which is that inflammation remains elevated and the disease is rarely cured. As an example, the prescribed anti-inflammatory treatment schedule could consist of taking successively reduced prednisone doses according to the following schedule: 40 mg/day for one week, 30 mg/day for one week, 20 mg/day for one week, 10 mg/day for one week, and 5 mg/day for one week.

In the tapering down of the doses, the hope is that suppression of the symptoms at the high doses may permit the patient's immune system to recover sufficiently at the subsequent low doses for it to overcome the disease on its own or reduce the patient's needs to lowered doses of the (toxic) drug(s) where side effects become more manageable or are measurably absent. The possibility of achieving full immunity reactivation, however, is remote in that the adrenal glands are rendered inactive as a result of administering the anti-inflammatory drugs. Any attempt to reactivate the adrenal gland requires a reduction in the ingested drug dose for an extended time, which increases the risk that the underlying disease will erupt again.

The relationship of inflammation to disease remains unknown and presents the classic chicken and egg problem—which came first? In other words, is inflammation the cause of the disease or a consequence of it. This lack of understanding has given rise to a treatment regimen that focuses on treating the symptoms instead of the underlying cause. The instant invention discloses a chemistry based model that analyzes the significance of inflammation in disease initiation and progression, and provides the basis for devising methods for treating the inflammatory disease(s).

SUMMARY OF THE INVENTION

Traditional treatments for inflammatory diseases include administering anti-inflammatory drugs to the patient. Following stabilization of symptoms, the drug doses are tapered down according to a prescribed schedule to minimize side effects, the consequence of which is that inflammation remains elevated and the disease is rarely cured. The focus traditionally has been on treating the symptoms. The instant invention, in contrast, treats the disease by managing and controlling its underlying cause.

By analyzing the abnormal biological and biochemical processes responsible for the inflammatory diseases as chemically reactive processes, this invention concludes that reductions in systemic inflammation will impede disease initiation and progression. Thus, alternate non-toxic ways to suppress inflammation and support the regulation of an active and healthy immune system are needed for controlling the inflammatory diseases.

While anti-inflammatory diets rich in antioxidants and anti-inflammatory compounds, such as nuts, brightly and variedly colored fruits and vegetables, turmeric, and ginger, or alternate medicine therapies including yoga are good long-term partial solutions for sound health, they do not offer the required benefit in the immediate future when a patient is faced with debilitating chronic inflammation-driven disease. However, exercise alone or in combination with diet modification has been shown in a number of studies to effectively reduce systemic inflammation and measured CRP levels. More recently, gastric bypass surgery too has been shown to reduce inflammation, likely the result of the associated weight reduction.

Consistent with the disease model of the instant invention, therapies that reduce inflammation, for example, anti-inflammatory drugs, exercise, and gastric bypass surgery, also impact disease progression. The inventor's personal experience has provided experimental verification and validation of the method claimed herein for successfully managing inflammatory diseases by reducing systemic inflammation and controlling it to acceptable levels. The non-drug therapies described can supplement the traditional toxic drug-based treatments to achieve low inflammation at sufficiently low drug maintenance doses where side effects are acceptably suppressed.

DETAILED DESCRIPTION OF INVENTION

Model

Because the onset of disease originates from an abnormal biological or biochemical process, which may be analyzed as a chemically reactive process, the following chemical reaction model serves to examine the significance of inflammation in diseases marked with systemic inflammation:

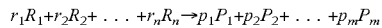

$$r_1R_1 + r_2R_2 + \ldots + r_nR_n \rightarrow p_1P_1 + p_2P_2 + \ldots + p_mP_m$$

where $r_1 \ldots r_n$ are the number of moles respectively of reactants $R_1 \ldots R_n$; $p_1, \ldots, p_m$ are the number of moles respectively of products $P_1, \ldots P_m$; and n and m are respectively the number of reactants and products.

Model Implications

Since the reactants in the above reaction model combine in specific proportions to produce products (which also form in specific proportions among themselves), if inflammation (i.e. one of the proteins or other biological species) associated with disease appears as a reactant, R, supporting the initiation and continued progression of the disease, a reduction in its quantity will lead to less consumption of the other reactant(s) and, consequently, less progression of the disease. Conversely, if systemic inflammation is the result of the underlying disease, i.e. it is a product of the reaction, then a low inflammation level means that less of the other products are also formed, or, in other words, less of the reactant species are consumed—again pointing to an arresting or slowing down of the disease.

A third possibility exists as well. The inflammation may be neither a reactant nor a product. It may simply mediate the reaction, for example, as a catalyst. Where the activation energy for the reaction causing the underlying disease may be high in the absence of inflammation, thereby inhibiting disease, increasing levels of inflammation with age and other factors could provide alternate lower activation energy pathways for such reactions to occur more readily, allowing the disease to propagate more rapidly to the patient's detriment because of increased disease reaction rate(s).

It is no coincidence that aggravated known risk factors for serious diseases also correlate with increased CRP levels. (See, Shoelson S. E. et al, Gastroenterology 2007; 132:2169-2180; Mehta J. L. et al, J Am Coll Cardiol 1998, 31:1217-122; Frohlich M. et al, Eur Heart J 2003; 24:1365-1372.) Because of this close correlation and the wide-ranging presence of inflammation in a broad spectrum of diseases, it is reasonable to conclude that the key risk factor for most such diseases is inflammation.

The goal of sound health vis a vis the inflammatory diseases, therefore, is to maintain low inflammation, which the model of the instant invention predicts would prevent inflammatory diseases from occurring or, where they have already occurred, slow down or arrest their further progression.

The salient prediction of the model is that irrespective of the exact role (reactant, product, or catalyst) that inflammation plays in the reaction(s) responsible for the underlying inflammatory disease, a reduction in inflammation will inhibit disease initiation and existing inflammatory diseases from progressing further. Thus, the key risk factor requiring control for impeding inflammatory diseases is systemic inflammation.

Consistent with the foregoing discussion, patients across a wide range of inflammatory diseases are known to respond favorably to anti-inflammatory drugs at elevated doses. (See also, Nicklas B. J. et al, CMAJ 2005, 172:1199-1209; Ford E. S., Epidemiology 2002, 13:561-568.) The reduction in inflammation from gastric bypass surgery explains why diabetes patients have seen their condition improve following surgery. (See, e.g. Agrawal V. et al, Surg Obes Relat Dis. 2009, 5:20-26; Schauer P. R. et al, N Engl J Med 2012, Mar. 26, 2012.) Indeed, the benefit of controlling heart disease with "an aspirin a day" too has been ascribed to aspirin's action as an anti-inflammatory agent at the low (81-162 mg/day) doses recommended (See, Oz M., The Dr. Oz Show: 28-Days to Prevent a Heart Attack. Available at http://www.doctoroz.com/videos/28-day-heart-disease-action-plan. Webpage accessed on Apr. 24, 2012.

The treatments for the vast majority of the inflammatory diseases involve administering anti-inflammatory drugs to suppress the immune response of the patient. Nearly all of such drugs, however, come with unacceptable side effects. This concern limits drug usage to the minimum doses that will control the symptoms at an appropriate level. Following stabilization of symptoms, the drug doses are tapered down to minimize side effects, the consequence of which is that inflammation remains elevated and the disease is rarely cured. The high drug dose treatments do, however, help in alleviating patients' symptoms in the short-term.

In the tapering down of the doses, the hope is that suppression of the symptoms at the high doses may permit the patient's immune system to recover sufficiently at the subsequent low doses for it to overcome the disease on its own or reduce the patient's needs to low doses of the drug(s) where the side effects become more manageable or are measurably absent. The possibility of achieving full immunity reactivation, however, is remote in that the adrenal glands are rendered inactive as a result of administering the anti-inflammatory drugs, which are mostly steroidal in origin. Any attempt to reactivate the adrenal gland requires a reduction in the ingested drug dose for an extended time, which increases the risk that the underlying disease will erupt again.

Thus, alternate, non-toxic, and preferably natural, ways to control inflammation and support the regulation of an active and healthy immune system are desired. Anti-inflammatory diets rich in antioxidants and anti-inflammatory compounds, such as nuts, brightly and variedly colored fruits and vegetables, turmeric, and ginger, or alternate medicine therapies including yoga are possible good long-term partial solutions for sound health, but they do not offer the required benefit in the immediate future when a patient is faced with debilitating chronic inflammation-driven disease. However, exercise alone or in combination with diet modification has been shown in a number of studies to effectively reduce systemic inflammation and measured CRP levels. More recently, gastric bypass surgery too has been shown to reduce inflammation, likely the result of the associated weight reduction. Thus, it is possible to devise a therapy that aims to drive down the systemic inflammation to acceptable levels through non-toxic means, such as exercise and diet, individually or preferably in combination, or gastric bypass surgery. These therapies are discussed by way of example and not by way of limitation.

A little less than five years ago, I had developed symptoms consisting mainly of dry cough, dyspnea, and fever. An early diagnosis of eosiniphilic pneumonia, gave way one and a half years later on the basis of high resolution computed tomography (HRCT) and video-assisted thoracic surgery (VATS) to a diagnosis of non-specific interstitial pneumonitis (NSIP), a progressive idiopathic inflammatory disease of the lung. NSIP is a sub-type of Idiopathic Pulmonary Fibrosis (IPF), comprising a group of interstitial pneumonias. (Magro, C. M. et al, Human Immmunol. 2006, 67:284-297) Consequently, both NSIP and IPF patients have been treated using the same toxic therapies, which have been largely ineffective. Despite having received continued treatment since an early eosiniphilic pneumonia diagnosis with tapered-down doses of prednisone (a powerful corticosteroid anti-inflammatory) from high levels of 30-40 mg/day, my systemic inflammation as measured by my CRP level continued to worsen, eventually approaching and exceeding levels in the teens of mg/l, and my continued symptoms to worsen.

Following the NSIP diagnosis, my tapered prednisone treatments were supplemented with 100 mg/day azathioprine and, subsequently, with 1800 mg/day N-Acetyl Cysteine (NAC). The three-drug (prednisone, azathioprine, and NAC) regimen was deemed to be superior to the two-drug (prednisone and azathioprine). Through all this, the CRP levels remained significantly elevated and, although the fever was controlled, the dry cough and dyspnea symptoms persisted, albeit at reduced levels. Efforts to taper down the prednisone to low (<10 mg/day) levels or reduce the azathioprine to <100 mg/day dose levels were unsuccessful, as the symptoms worsened to unacceptable levels.

Indeed, a study recently published in the New England Journal of Medicine had concluded that treatment with this combination of drugs may be inadvisable as it is therapeutically ineffective and, in fact, may increase the patient's mortality. (Raghu G. et al., N Engl J Med 2012; 366:1968-1977). In the same continuing study, these investigators further determined that "As compared with placebo, acetylcysteine offered no significant benefit with respect to the preservation of FVC [i.e., lung capacity] in patients with idiopathic pulmonary fibrosis . . . " (Martinez F. J. et al., N Engl J Med 2014; 370:2093-2101; Abstract). Not surprisingly, the two-drug treatment has been, likewise, ineffective. Indeed, as stated in an October 2011 National Institutes of Health (NIH) press release "IPF is a progressive and currently incurable disease . . . " (emphasis added)

As a first early approach towards stabilizing my symptoms and improving my condition in the absence of an effective treatment regimen, I enriched my diet with antioxidants and anti-inflammatory compounds, including nuts (peanuts, almonds, and walnuts) and brightly and variedly colored fruits and vegetables, turmeric, and ginger, However, the effects of this change in diet on my condition and measured CRP levels remained unnoticeable over a period of a few months, and the CRP levels and symptoms continued to degrade.

Since exercise, four to five days weekly, both aerobic and resistance, has been shown in a number of studies to reduce systemic inflammation and measured CRP levels, I started a regimen of regular moderate level exercise soon after my NSIP diagnosis. Almost immediately, within three to six months, the benefits from exercise started to become apparent. I ramped up the intensity of the workout, to about 150-180 cumulative minutes per week on the treadmill over a period of several months, I supplemented these workouts with about ten to fifteen minutes of sit-ups and weight training.

Over the span of about nine months, my CRP-levels gradually reduced from their high values, reaching and stabilizing at levels of between 2 and about 3 mg/l, and my symptoms attenuated concurrently. Annual HRCT examinations confirmed that the lung microstructure had remained reasonably stable over at least two years following the initiation of my exercise and diet regimen. During this period, the complete blood count (CBC) blood analyses remained close to normal, my pulmonary function tests (PFTs) remained reasonably stable, and I was successfully able to reduce my dependence on medication over time. The reduction in my dose levels was gradual to allow my immune system and adrenal glands to adjust and recover at the reduced inflammation levels, aided by exercise and diet. Eventually, for about a year and a half, my condition stabilized on 5 mg/day of prednisone, 1800 mg/day NAC, and 75 mg/day azathioprine. More recently, I was able to further lower my azathioprine dose to 50 mg/day with little to no perceptible downside effects.

My personal experience validates the instant model's prediction that irrespective of the exact role (reactant, product, or catalyst) that inflammation plays in the reaction(s) responsible for the underlying disease, a reduction in inflammation levels will impede the disease from progressing further.

Thus, the method of treating and managing the inflammatory diseases is reasonably straightforward. An objective and accepted test for measuring systemic inflammation needs to be identified, and the patient's level of inflammation verified as higher than normal. One such widely available test measures the CRP level in the blood of the patient. Tests for other biological markers of inflammation may also be used instead of, or in addition to, the measurement of the CRP level and are within the scope of the instant invention. The treatment focuses on reducing the patient's inflammation to levels within or below the normal range, i.e., values typical or below that of the population free from the chronic inflammatory disease(s).

Depending on the severity of the disease at the onset of treatment, the initial stages of treatment likely require high doses of the available anti-inflammatory drugs, which, although toxic, help quickly alleviate patient symptoms in the near-term. After stabilization of the symptoms, the toxic drug levels are incrementally stepped down, even as non-toxic ways are used to stabilize the patient's symptoms and further lower the patient's inflammation level at each of the successively reduced toxic drug dose levels.

The tapering of the dose in the instant invention is performed incrementally in discrete steps, so that the patient's symptoms and inflammation are stabilized at each lower level before the next incremental reduction in the toxic drug dose is attempted. Thus, unlike the traditional treatments where the time for taking each successively lower dose follows a prescribed schedule, the key distinction of the method of the instant invention is that the duration for taking the drug at each dose level is determined by the stabilization of the patient's symptoms and inflammation level at that dose. This controlled stepped reduction in the toxic drug dose continues preferably until the CRP value is reduced to below 3 mg/l or until no further CRP reduction is possible, as indicated, by the inability of the patient to maintain the improved condition with the alternate therapy(ies) at even lower drug doses. Once the CRP value is reduced to below 3 mg/l, further treatment with the toxic drug is preferably discontinued, if possible, and the patient's inflammation maintained below 3 mg/l using just the non-toxic therapy. Depending on the patient's disease and its severity, the total time span over which such stepping down of the dose is accomplished could range from a few to several months or more.

Moderate levels of aerobic and resistance exercises, each session lasting in the range of 20 minutes to one hour (i.e. cumulatively on the order of 100 to 300 minutes per week), and diets rich in anti-inflammatory compounds and antioxidants are good examples of effective non-toxic ways (that are also natural) for reducing inflammation and stabilizing the symptoms at each of the incrementally lowered doses of the toxic drugs. Use of gastric bypass surgery, particularly as regards patients who are overweight, and non-steroidal drugs can also help stabilize the patient at the lowered toxic drug doses, but care must be taken to avoid any complications associated with the surgery or the intake of the non-steroidal drugs. All of these treatment options are within the spirit and scope of the invention herein and its claims.

The potential benefits to society from implementing the method of the instant invention are considerable. Until better non-toxic anti-inflammatory drugs are developed, exercise and diet can be readily factored into one's daily routine (and gastric bypass surgery possibly made available as an extreme option) as preventive or even corrective measures for addressing an overwhelming number of age-related inflammation-associated diseases. Inflammation levels typically rise with age in humans, and its elevated levels are likely a significant factor in predisposing people to increased susceptibility for affliction with one or more of an overwhelming number of chronic age-related inflammation-driven diseases.

The above proposed disease analysis and treatment methodology lays the foundation for anew approach to disease characterization and management. Although the disease model of the present invention has been expressly applied and demonstrated for inflammatory diseases. the model is generic and is equally applicable to non-inflammatory diseases. As would be obvious from the model herein to one skilled in the art, for each disease one simply needs to identify at least one unique, measurable disease-characteristic biological marker that lends itself to therapeutic control. The identification and control of such biological markers would provide the practitioners with alternative and effective methods for disease management across a wide spectrum of diseases, some possibly even considered incurable at present. The scope of the instant invention is to be limited only by the claims and not by the description herein.

I claim:

1. A method of treating non-specific interstitial pneumonitis in a patient comprising the steps of:
   (i) confirming that the patient's C-Reactive Protein (CRP) concentration in the blood is 3 mg/l or more;
   (ii) stabilizing the patient's symptoms with prednisone and azathioprine;
   (iii) stepping down the prednisone and azathioprine drug doses incrementally;
   (iv) stabilizing the patient's symptoms and inflammation after each step down of the prednisone and azathioprine drug doses using a non-toxic therapy wherein the non-toxic therapy is selected from the group comprising aerobic exercise and resistance exercise; and
   (v) continuing said incremental stepping down of the prednisone and azathioprine drug doses using said non-toxic therapy until the inflammation is reduced to a CRP value of below 3 mg/l.

2. The method of claim 1, wherein the non-toxic therapy further includes an anti-inflammatory diet.

3. A method of treating non-specific interstitial pneumonitis in a patient comprising the steps of:
   (i) confirming that the patient's C-Reactive Protein (CRP) concentration in the blood is 3 mg/l or more;
   (ii) stabilizing the patient's symptoms with prednisone and azathioprine;
   (iii) stepping down the prednisone and azathioprine drug doses incrementally;
   (iv) stabilizing the patient's symptoms and inflammation after each step down of the prednisone and azathioprine drug doses using exercise; and
   (v) continuing said incremental stepping down of the prednisone and azathioprine drug doses using said exercise until the inflammation is reduced to a CRP value of below 3 mg/l.

4. A method of treating non-specific interstitial pneumonitis in a patient comprising the steps of:
   (i) stabilizing the patient's symptoms with prednisone and azathioprine;
   (ii) stepping down the prednisone and azathioprine drug doses and reducing the patient's inflammation using exercise; and
   (iii) continuing said stepping down of the prednisone and azathioprine drug doses with said exercise until the inflammation is reduced to a CRP value of below 3 mg/l.

* * * * *